(12) United States Patent
Göhler et al.

(10) Patent No.: US 10,036,746 B2
(45) Date of Patent: *Jul. 31, 2018

(54) METHOD FOR THE DIAGNOSIS OF NEUROMYELITIS OPTICA (71) Applicant: PROTAGEN AG, Dortmund (DE)

(72) Inventors: Heike Göhler, Bochum (DE); Petra Rengers, Münster (DE); Angelika Lüking, Bochum (DE); Stefan Müllner, Langenfeld (DE)

(73) Assignee: PROTAGEN AG, Dortmund (DE)

( * ) Notice: Subject to any disclaimer, the term of this patent is extended or adjusted under 35 U.S.C. 154(b) by 0 days.

This patent is subject to a terminal disclaimer.

(21) Appl. No.: 15/404,293

(22) Filed: Jan. 12, 2017

(65) Prior Publication Data

US 2017/0115288 A1    Apr. 27, 2017

Related U.S. Application Data

(62) Division of application No. 14/780,617, filed as application No. PCT/EP2014/056383 on Mar. 28, 2014, now Pat. No. 9,588,115.

(30) Foreign Application Priority Data

Mar. 28, 2013  (EP) .................................... 13161822

(51) Int. Cl.
  *C07K 14/00* (2006.01)
  *G01N 33/564* (2006.01)
(52) U.S. Cl.
  CPC ..... *G01N 33/564* (2013.01); *G01N 2800/285* (2013.01); *G01N 2800/50* (2013.01); *G01N 2800/52* (2013.01); *G01N 2800/56* (2013.01)

(58) Field of Classification Search
  None
  See application file for complete search history.

(56) References Cited

U.S. PATENT DOCUMENTS 6,812,339 B1   11/2004   Venter et al.
2008/0145870 A1   6/2008   Lennon et al.

FOREIGN PATENT DOCUMENTS

| CN | 101576558 A | 11/2009 |
| EP | 1700120 A2 | 9/2006 |
| WO | WO-2005/051178 A2 | 6/2005 |
| WO | WO-2007/068982 A2 | 6/2007 |
| WO | WO-2012/149259 A1 | 11/2012 |

OTHER PUBLICATIONS

Waters, P. J., et al., "Serologic Diagnosis of NMO—A Multicenter Comparison of Aquaporin-4-IgG Assay", Neurology, 2012, vol. 78, pp. 665-671.

(Continued)

*Primary Examiner* — Adam Weidner
*Assistant Examiner* — Aurora M Fontainhas
(74) *Attorney, Agent, or Firm* — Drinker Biddle & Reath LLP (57) ABSTRACT

The present invention relates to a method for the diagnosis and/or risk stratification of neuromyelitis optica (abbreviated NMO), wherein a determination from a body sample of a patient/test subject is performed by means of artificial aquaporin-4 peptides. The invention further relates to a kit and to new artificial aquaporin-4 peptides as such.

6 Claims, 3 Drawing Sheets

(56) References Cited

OTHER PUBLICATIONS

Waters, P., et al., "Multicentre Comparison of a Diagnostic Assay: Aquaporin-4-Antibodies in Neuromyelitis Optica", J. Neurol. Neurosurg, Psychiatry, 2016, vol. 0, pp. 1-11.
International Search Report for PCT/EP2014/056383 dated Aug. 19, 2014.
Yu, X., et al., "Identification of Peptide Targets in Neuromyelitis Optica", Journal of Neuroimmunology, 2011, vol. 236, pp. 65-71.

FIGURE 1:

aquaporin-4 isoform a [Homo sapiens]
Sequence ID: ref|NP_001641.1| Length: 323 Number of Matches: 1
▶ See 7 more title(s)

Range 1: 1 to 323  GenPept  Graphics                          ▼ Next Match  ▲ Previous Match

| Score | Expect | Method | Identities | Positives | Gaps |
|---|---|---|---|---|---|
| 321 bits(822) | 8e-109 | Compositional matrix adjust. | 193/323(60%) | 193/323(59%) | 115/323(35%) |

```
Query    1   MSDRPTARRWGKCGPLCTRENIMVAFKGVWTQG----------------------PGFTINWG    41
             MSDRPTARRWGKCGPLCTRENIMVAFKGVWTQ                        G TINWG
Sbjct    1   MSDRPTARRWGKCGPLCTRENIMVAFKGVWTQAFWRAYTAEFLAMLIFVLLSLGSTINWG    60

Query   42   GTEKPLFVD---------------GPGPGGHINPAVTVAMVCTRKIS----------    73
             GTEKPLFVD              G  GGHINPAVTVAMVCTRKIS
Sbjct   61   GTEKPLFVDRVLISLCFGLSIATNVQCFGHISGGHINPAVTVAMVCTRKISIAKSVFYIA   120

Query   74   ----------GPGPLVTPPSVVGGLGVTMVHGN----GPG-------------------PCDS   103
                       G  LVTPPSVVGGLGVTMVHGN     G G                   CDS
Sbjct  121   AQCLGAIIGAGILYLVTPPSVVGGLGVTMVHGNLTAGHGLLVELIITFQLVFTIFASCDS   180

Query  104   KRTDVTGSI-------------------GPGPNPARSFGPAVINGNNENHW-----GP----   137
             KRTDVTGSI                  G   NPARSFGPAVINGNNENHW     GP
Sbjct  181   KRTDVTGSIALAIGFSVAIGHLFAINYTGASNPARSFGPAVINGNNENHWIYWVGPIIG    240

Query  136   ------------GPDVEFKRRFKEAFSKAAQQTKGSYMEVEDNRSQVETDDLILKPGVVH    185
                         GDVEFKRRFKEAFSKAAQQTKGSYMEVEDNRSQVETDDLILKPGVVH
Sbjct  241   AVLAGGLYEYVFCPDVEFKRRFKEAFSKAAQQTKGSYMEVEDNRSQVETDDLILKPGVVH   300

Query  186   VIDVDRGEEKKGKDQSGEVLSSV                                        208
             VIDVDRGEEKKGKDQSGEVLSSV
Sbjct  301   VIDVDRGEEKKGKDQSGEVLSSV                                        323
```

METHOD FOR THE DIAGNOSIS OF NEUROMYELITIS OPTICA

RELATED APPLICATIONS

This application is a divisional of patent application Ser. No. 14/780,617 filed on Sep. 28, 2015, which is a national stage application (under 35 U.S.C. § 371) of PCT/EP2014/056383, filed Mar. 28, 2014, which claims benefit of European Application No. 13161822.5, filed Mar. 28, 2013. The entire content of each above application is hereby incorporated by reference in its entirety.

SUBMISSION OF SEQUENCE LISTING

The Sequence Listing associated with this application is filed in electronic format via EFS-Web and hereby incorporated by reference into the specification in its entirety. The name of the text file containing the Sequence Listing is Sequence_Listing_074027_0033_01. The size of the text file is 7 KB, and the text file was created on Jan. 11, 2017.

FIELD OF THE INVENTION

The present invention relates to a method for the diagnosis and/or risk stratification of neuromyelitis optica (abbreviated NMO), wherein a determination from a body sample of a patient/test subject is performed with the aid of artificial aquaporin-4 peptides. The invention further relates to a kit and to new artificial aquaporin-4 peptides as such.

DESCRIPTION OF RELATED ART

Early diagnosis and differentiation of NMO, in particular for distinction from multiple sclerosis (MS), is necessary in order to provide suitable treatment for NMO.

In the prior art, human aquaporin-4 is described as an autoantigen for the detection and diagnosis of NMO (US 20080145870 and EP 1700120B1). In this connection, it is known that autoantibodies that specifically bind to human aquaporin-4 of the type depicted in SEQ ID NO: 1 can be detected in the serum of NMO patients. A corresponding ELISA kit is available on the market (V. A. Lennon et al. A serum autoantibody marker of neuromyelitis optica: distinction from multiple sclerosis, Lancet 2004 364(9451): 2106-2112; V. A. Lennon et al. IgG marker of optic-spinal multiple sclerosis binds to the aquaporin-4 water channel, The Journal of Experimental Medicine 2005 202: 473-477 B; G. Weinshenker et al. Neuromyelitis optica IgG predicts relapse after longitudinally extensive transverse myelitits. Annals of Neurology 2006 59: 566-569).

Another disadvantage of the known diagnostic methods that use the previously known markers, however, is that early and complete detection of high-risk patients is inadequate and therefore risk stratification cannot be adequately performed. A problem addressed by the invention is therefore that of developing a method for the diagnosis and risk stratification of NMO that provides for an improved detection of high-risk patients, in particular in the point-of-care area.

It is disadvantageous in the prior art that sufficient sensitivity and/or specificity is usually not achieved with a rapid test in the point-of-care area.

BRIEF SUMMARY OF THE INVENTION

The problem addressed by the present invention is therefore that of providing a method for the in vitro diagnosis and/or risk stratification of NMO.

The problem is solved by a method for the diagnosis and risk stratification of NMO, wherein a determination of autoantibodies from a body sample is performed with the aid of artificial aquaporin-4 peptides (the method according to the invention in the following).

Surprisingly, artificial aquaporin-4 peptides now exhibit high sensitivity and specificity for the diagnosis of NMO.

DETAILED DESCRIPTION OF THE INVENTION

Within the scope of this invention, "aquaporin-4" is understood to mean a protein which participates in the regulation of the water and electrolyte balance primarily in the central nervous system, functioning as a water channel in cell membranes. These water channels are found particularly frequently in the sections that are classically affected by NMO. A suitable aquaporin-4 is depicted in SEQ ID NO: 1 with 323 amino acids. Autoantibodies to the autoantigen aquaporin-4 are formed by peripheral plasma cells. After binding to their target antigen, said autoantibodies result in complement activation with local inflammatory demyelination and necrosis. The clinical picture corresponds to optic neuritis and local myelitis over three or more spinal segments with predominant localization at or in the vicinity of the blood-brain barrier.

The term "NMO" according to the invention (synonym: Devic's syndrome) relates to an inflammatory autoimmune disease of the central nervous system. This affects, in particular, the spinal marrow (myelitis) and the optic nerves (optic neuritis). The disease manifests as paralysis of the arms and legs, reduced sensation, and loss of bladder and bowel control, as well as blindness. Histologically, the affected tissue contains perivascular deposits of autoantibody immunoglobulins and complement factors. The autoantibodies that form are specific for NMO and can be used for the differential diagnosis of multiple sclerosis with the aid of the autoantigen human aquaporin-4.

Artificial aquaporin-4 peptides are used within the scope of the present invention, wherein, proceeding from SEQ ID NO: 1, the artificial aquaporin-4 peptides additionally contain at least one spacer having 2 to 30 amino acids as compared to SEQ ID NO: 1, preferably 2 to 20 amino acids, particularly preferably 2 to 10 amino acids, wherein the spacer does not contain any amino acid sequence of SEQ ID NO: 1.

In a preferred embodiment of the invention, the spacer consists of hydrophilic amino acids (serine, threonine, etc.).

In addition, helix-breaking amino acids are preferred, such as, in particular, proline (P) and glycine (G) (in the following: GP spacer).

In addition, the spacer can contain any amino acid as well as artificial amino acids.

Other suitable artificial aquaporin-4 peptides can be:

In another particular embodiment, at least one spacer is inserted/contained between amino acids 32 and 253 of SEQ ID NO: 1. In addition, it is preferred that at least one spacer is inserted/contained in the regions of the transmembrane domains, selected from the sequence sections of amino acids 33 to 55, 70 to 92, 112 to 134, 154 to 176, 189 to 211 and 231 to 253 of SEQ ID NO: 1.

In another preferred embodiment of the invention, proceeding from SEQ ID NO: 1, amino acids can be omitted or deleted such that sequences can be obtained which at least contain the following subsequences selected from the group SDRPTARRWGKCGP (SEQ ID NO: 3), GGTEKPLPVD (SEQ ID NO: 4), CDSKRTD (SEQ ID NO: 5), NPARSFG (SEQ ID NO: 6), EFKRRFKEAFSKAA (SEQ ID NO: 7) or EFKRRFKEAFSKAAQQ (SEQ ID NO: 8) or EFKRRFKEAFSKAAQQTKG (SEQ ID NO: 9), DVDRGEEKKGKDQSGE (SEQ ID NO: 10) and comprise at least one spacer according to the invention.

The invention also relates to autoantigens for the diagnosis of NMO consisting of an amino acid sequence (polypeptide), wherein amino acids are omitted or deleted as compared to the SEQ ID NO: 1, but at least the subsequences SDRPTARRWGKCGP (SEQ ID NO: 3), GGTEKPLPVD (SEQ ID NO: 4), CDSKRTD (SEQ ID NO: 5), NPARSFG (SEQ ID NO: 6), EFKRRFKEAFSKAA (SEQ ID NO: 7) and/or EFKRRFKEAFSKAAQQ (SEQ ID NO: 8) and/or EFKRRFKEAFSKAAQQTKG (SEQ ID NO: 9), DVDRGEEKKGKDQSGE (SEQ ID NO: 10) are contained and the polypeptide that is obtained consists of at most 250 amino acids, preferably at most 220 amino acids.

The invention also relates to autoantigens for the diagnosis of NMO consisting of an amino acid sequence (polypeptide), which contain the following subsequences selected from the group SDRPTARRWGKCGP (SEQ ID NO: 3), GGTEKPLPVD (SEQ ID NO: 4), CDSKRTD (SEQ ID NO: 5), NPARSFG (SEQ ID NO: 6), EFKRRFKEAFSKAA (SEQ ID NO: 7) and/or EFKRRFKEAFSKAAQQ (SEQ ID NO: 8) and/or EFKRRFKEAFSKAAQQTKG (SEQ ID NO: 9), DVDRGEEKKGKDQSGE (SEQ ID NO: 10) and comprise at least one spacer which contains 2 to 30 amino acids, preferably 2 to 20 amino acids, particularly preferably 2 to 10 amino acids, and the polypeptide that is obtained consists of at most 250 amino acids, preferably at most 220 amino acids, wherein the spacer does not contain any amino acid sequence of SEQ ID NO: 1

A particularly preferred embodiment is SEQ ID NO: 2, wherein a plurality of GP spacers are contained therein.

In addition, the invention relates to the use of these autoantigens according to the invention for the diagnosis of NMO according to one of the embodiments mentioned above or in the following.

A person skilled in the art is capable of producing corresponding amino acid sequences according to the invention, i.e. artificial aquaporin-4 peptides, e.g. fully synthetically by means of Merrifield synthesis (Weng C. Chan, Peter D. White: Fmoc Solid Phase Peptide Synthesis: A Practical Approach. Oxford University Press, Oxford/New York 2000).

It is particularly preferred, however, to provide corresponding cDNA, e.g. proceeding from a cDNA, such as, e.g. SEQ ID NO: 1 from EP1700120B1, wherein corresponding cDNA can be manufactured for the artificial aquaporin-4 peptides according to the invention. Corresponding techniques/specifications are found, e.g., in Sambrook et al, "Molecular Cloning, A laboratory handbook, 2nd edition (1989), CSH press, Cold Spring Harbor, N.Y.; Frederick M. Ausubel, Short protocols in molecular biology: a compendium of methods from current protocols in molecular biology, Volume 1, Wiley, 2002.

Such a spacer based on DNA can be inserted into the cDNA by means of ligation, for example.

As mentioned above, the spacers are preferably inserted in the aforementioned regions of the transmembrane domains of SEQ ID NO: 1. This results, according to the invention, in an increased sensitivity of autoantibodies of these artificial aquaporin-4 peptides that are obtained as compared to the known aquaporin-4, probably due to the omission of helices in the quaternary structure. This is also advantageous according to the invention, since a simplified genetic expression of the artificial aquaporin-4 peptides in a host, such as *E. coli*, is made possible.

Particularly advantageously, the method according to the invention provides for a reliable stratification in cases, in particular, of emergency and/or intensive care medicine. The method according to the invention therefore makes it possible to make clinical decisions that can result in rapid therapeutic success and can save lives. Such clinical decisions also comprise continued treatment with pharmaceuticals for handling or treating NMO.

Therefore, the invention also relates to a method for the diagnosis and/or risk stratification of NMO patients for the purpose of making clinical decisions, such as continued handling and treatment with pharmaceuticals, preferably in time-critical intensive care medicine or emergency medicine, including the decision to hospitalize the patient.

In another preferred embodiment, the method according to the invention therefore relates to the therapy control of NMO.

In another preferred embodiment of the method according to the invention, the diagnosis and/or risk stratification is carried out for purposes of prognosis, differential-diagnostic early detection and detection, assessing severity, and assessing the course of the disease in association with treatment.

In another preferred embodiment, the invention relates to a method for the in vitro diagnostics for the early diagnosis or differential diagnosis or prognosis of NMO, wherein a determination of autoantibodies from a body sample with the aid of artificial aquaporin-4 peptides is carried out on or by a patient to be examined.

In an embodiment of the method according to the invention, a body sample, in particular tissue or bodily fluid, preferably blood, either whole blood or serum or available plasma, is taken from the patient to be examined and the diagnosis is carried out in vitro/ex vivo, i.e. outside of the human or animal body. Due to the determination of autoantibodies from a body sample with the aid of artificial aquaporin-4 peptides, high sensitivity and specificity are obtained and the diagnosis or risk stratification can be carried out on the basis of the quantity available in at least one patient sample.

The quantity of autoantibodies can be determined, for example by means of radiolabeled or biotinylated artificial aquaporin-4 peptides (e.g. S(35) method or the like). Artificial aquaporin-4 peptides that remain free can be extracted, for example. In addition, autoantibodies bound to artificial aquaporin-4 peptides can be detected via fluorescence with the aid of anti-autoantibodies.

In another embodiment of the invention, the method according to the invention can be carried out within the framework of an in vitro diagnosis by means of parallel or simultaneous determinations with the aid of the artificial aquaporin-4 peptides (e.g., multititer plates having 96 or more cavities), wherein the determinations are carried out on at least one patient sample.

In another embodiment, the method according to the invention and its determinations can be carried out by means of a rapid test (e.g., lateral flow test or point-of-care), either as a single determination or a multiparameter determination. In a particularly preferred embodiment, this is a rapid test or a device that is suitable for use in emergency diagnostics.

Another problem is that of providing a corresponding diagnostic device or its use for carrying out the method according to the invention.

Within the scope of this invention, such a diagnostic device is understood to be, in particular, an array or an assay (e.g., immunoassay, ELISA, etc.), in the broadest sense a device for carrying out the method according to the invention.

The detection and the quantification of bound autoimmune antibodies on the artificial aquaporin-4 peptides according to the invention can also be carried out with the aid of other protein diagnostic methods commonly known to a person skilled in the art, in particular using radiolabeled or enzyme- or fluorescence-labeled antibodies. Examples include, in particular, bioanalytical methods which are suitable therefor, such as, for example immunohistochemistry, antibody arrays, Luminex, ELISA, immunofluorescence, radioimmunoassays, and other suitable bioanalytical methods, such as for example mass-spectrometric methods, e.g. MRM (multi-reaction monitoring) or AQUA (absolute quantification), with the aid of which the autoimmune antibodies are quantitatively measured and the particular detection can be carried out.

The invention also relates to a kit for the diagnosis and/or risk stratification of NMO, containing artificial aquaporin-4 peptides including detection reagents and, optionally, auxiliary agents. Such detection reagents comprise, e.g. antibodies, beads, etc.

The following examples and figures are provided to explain the invention in greater detail, although the invention is not limited to these examples and figures.

Figure 1:
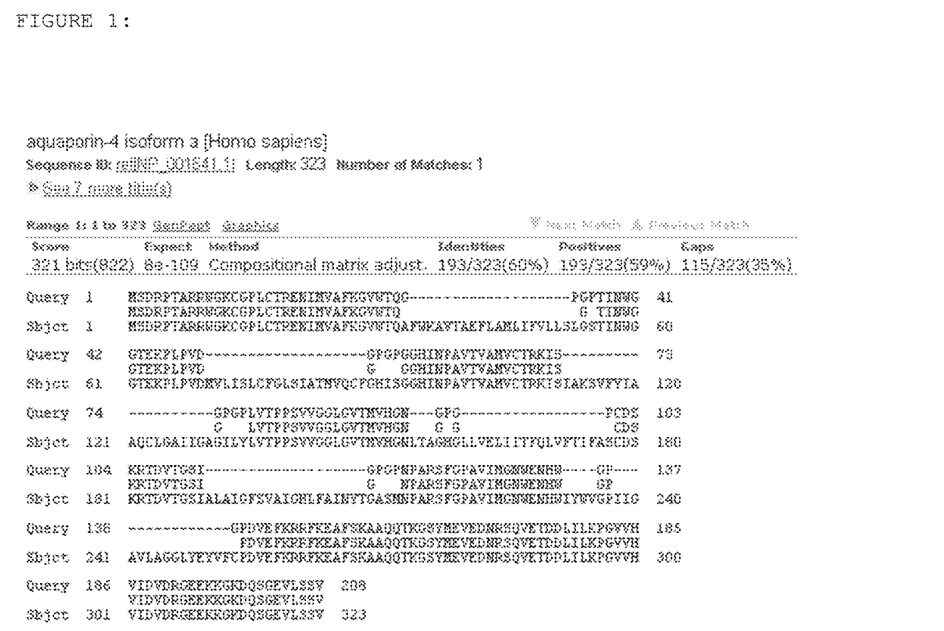
FIG. 1 shows the structural differences between SEQ ID NO: 1 (human aquaporin-4; "Sbjct") and SEQ ID NO: 2 ("Query") according to the invention, containing GP spacers and the preferred subsequences.
Figure 2A:
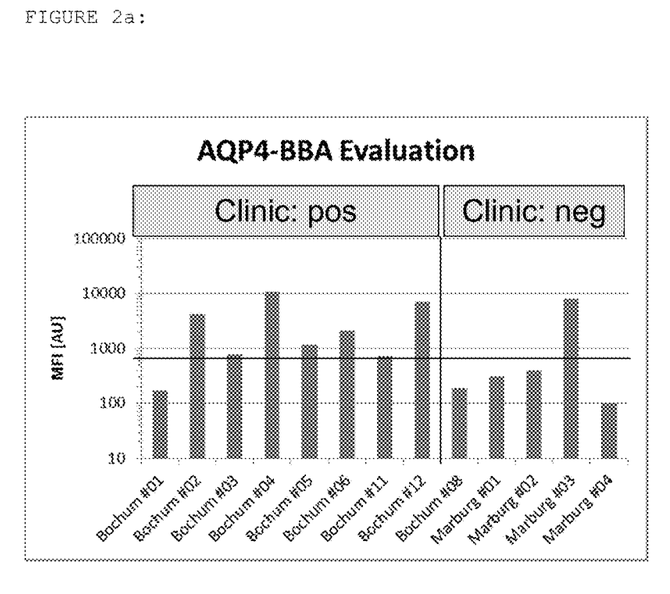
FIG. 2a shows the diagnosis of NMO on the basis of 8 positive and 5 negative patient samples (hospital) by means of a Luminex bead assay using SEQ ID NO: 2.
Figure 2B:
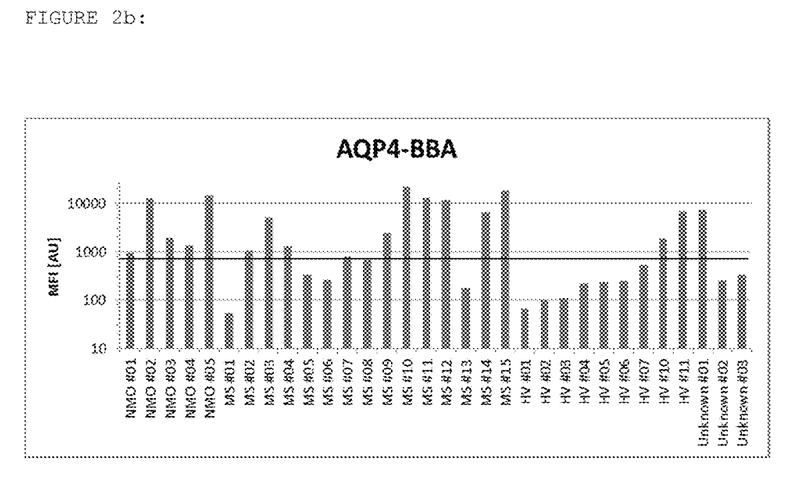
FIG. 2b shows the stratification of NMO patients ("NMO") versus multiple sclerosis patients (MS) and healthy patients (HV) by means of a Luminex bead assay using SEQ ID NO: 2.
Figure 3:
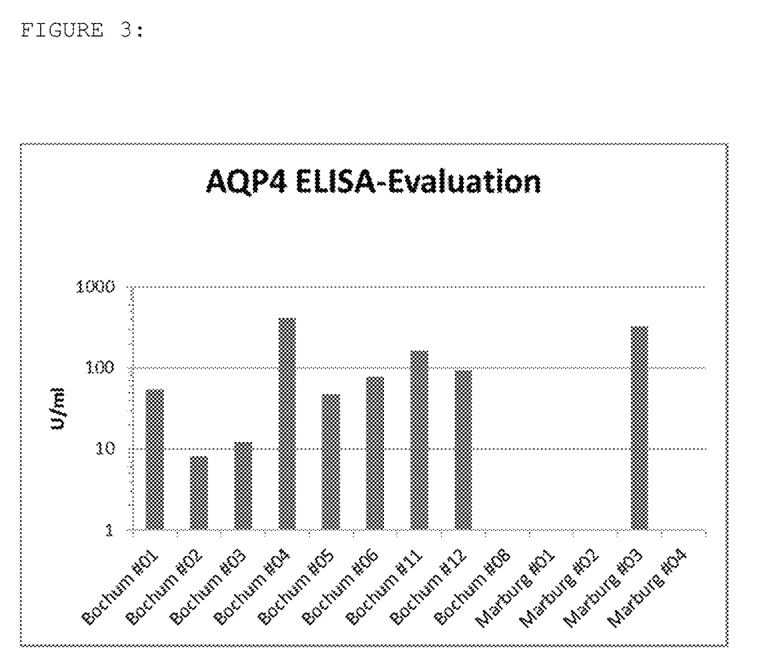
FIG. 3 shows the diagnosis of NMO on the basis of 9 positive and 4 negative patient samples (hospital) by means of an ELISA assay according to the aforementioned example using SEQ ID NO: 2.

FIG. 1 shows the structural differences between SEQ ID NO: 1 (human aquaporin-4) and SEQ ID NO: 2 according to the invention, containing GP spacers and the preferred subsequences.

Examples

The method according to the invention can be carried out, e.g. in a manner analogous to Lennon 2004, 2005 (supra).

Calibrators, some of which are positive controls and some of which are negative controls, are dispensed in a microtiter plate (96 wells and more).

An artificial aquaporin-4 according to SEQ ID NO: 2, according to the invention, is used as the autoantigen, e.g. biotinylated or radiolabeled and dissolved in buffer (e.g. PBS), and is stirred.

In the case of biotinylated artificial aquaporin-4 according to SEQ ID NO: 2, an autoantibody binding detection can take place by means of streptavidin peroxidase (see, e.g. Prescott, L. M.; Harley, J. P.; Klein, D. A.: *Microbiology.* 5th Edition. McGraw Hill, Boston 2002).

50 μl NMO patient serum are added in a microtiter plate, each with controls and calibrators.

25 μl of a solution of biotinylated artificial aquaporin-4 according to SEQ ID NO: 2 are added to each well.

The ELISA prepared in this manner is washed three times with a washing solution. Next, 100 μl streptavidin peroxidase is added to the wells and the wells are shaken and washed, then a peroxidase substrate is added to the wells and the wells are incubated. A photometric evaluation is then carried out by reference to a calibration curve.

The method according to the invention can also be carried out using a common radioimmunoassay (RIA).

FIG. 2*a* shows the diagnosis of NMO on the basis of 8 positive and 5 negative patient samples (hospital) by means of a Luminex bead assay using SEQ ID NO: 2, wherein, given an ascertained threshold value of 675 MFI (median fluorescence intensity), it was possible to correctly test 85% of the clinical patients.

FIG. 2*b* shows the stratification of NMO patients ("NMO") versus multiple sclerosis patients (MS) and healthy patients (HV) by means of a Luminex bead assay using SEQ ID NO: 2, wherein 100% of the NMO patients were detected given an ascertained threshold value of 675 MFI.

FIG. 3 shows the diagnosis of NMO on the basis of 9 positive and 4 negative patient samples (hospital) by means of an ELISA assay according to the aforementioned example using SEQ ID NO: 2, wherein it was possible to correctly test 92% of the clinical patients.

We claim:

1. A method for in vitro diagnosis of neuromyelitis optica (NMO), risk stratification of NMO, prognosis of NMO, differential-diagnostic early detection of NMO, assessing severity of NMO and/or assessing the course of NMO in association with treatment, the method comprising measuring the autoantibodies of aquaporin-4 from a body sample of a patient by contacting the autoantibodies with the artificial aquaporin-4 autoantigen, said autoantigen consisting of the amino acid sequence of SEQ ID NO: 2.

2. A method for in vitro diagnosis of neuromyelitis optica (NMO), risk stratification of NMO, prognosis of NMO, differential-diagnostic early detection of NMO, assessing severity of NMO and/or assessing the course of NMO in association with treatment, the method comprising measuring the autoantibodies of aquaporin-4 from a body sample of a patient by contacting the autoantibodies with the artificial aquaporin-4 autoantigens, said autoantigens consisting of an amino acid sequence, which contain a sequence selected from the group consisting of SDRPTARRWGKCGP (SEQ ID NO: 3), GGTEKPLPVD (SEQ ID NO: 4), CDSKRTD (SEQ ID NO: 5), NPARSFG (SEQ ID NO: 6), EFKRRFKEAFSKAA (SEQ ID NO: 7), EFKRRFKEAFSKAAQQ (SEQ ID NO: 8), EFKRRFKEAFSKAAQQTKG (SEQ ID NO: 9), and DVDRGEEKKGKDQSGE (SEQ ID NO: 10), and comprise at least one spacer, which contains 2 to 30 amino acids, 2 to 20 amino acids, or 2 to 10 amino acids, and the polypeptide that is obtained consists of at most 250 amino acids, wherein the spacer does not contain any amino acid sequence of SEQ ID NO: 1.

3. A method for in vitro diagnosis of neuromyelitis optica (NMO), risk stratification of NMO, prognosis of NMO, differential-diagnostic early detection of NMO, assessing severity of NMO and/or assessing the course of NMO in association with treatment, the method comprising measuring the autoantibodies of aquaporin-4 from a body sample of a patient by contacting the autoantibodies with the artificial aquaporin-4 autoantigens, said autoantigens consisting of an amino acid sequence, which contain a sequence selected from the group consisting of SDRPTARRWGKCGP (SEQ ID NO: 3), GGTEKPLPVD (SEQ ID NO: 4), CDSKRTD (SEQ ID NO: 5), NPARSFG (SEQ ID NO: 6), EFKRRFKEAFSKAA (SEQ ID NO: 7), EFKRRFKEAFSKAAQQ (SEQ ID NO: 8), EFKRRFKEAFSKAAQQTKG (SEQ ID NO: 9), and DVDRGEEKKGKDQSGE (SEQ ID NO: 10), and comprise at least one spacer which contains 2 to 30 amino acids, 2 to 20 amino acids, or 2 to 10 amino acids, and the polypeptide that is obtained consists of at most 250 amino acids, wherein the spacer does not contain any amino acid sequence of SEQ ID NO: 1, or the amino acid sequence of SEQ ID NO: 2.

4. The method of any one of claim 1, 2 or 3, wherein the patient is a symptomatic patient.

5. The method of any one of claim 1, 2 or 3, wherein the patient is an asymptomatic patient.

6. The method of any one of claim 1, 2 or 3, wherein the measurement is performed with an array or immunoassay.

* * * * *

```
                        SEQUENCE LISTING

<160> NUMBER OF SEQ ID NOS: 10

<210> SEQ ID NO 1
<211> LENGTH: 323
<212> TYPE: PRT
<213> ORGANISM: Homo sapiens

<400> SEQUENCE: 1

Met Ser Asp Arg Pro Thr Ala Arg Arg Trp Gly Lys Cys Gly Pro Leu
1               5                   10                  15

Cys Thr Arg Glu Asn Ile Met Val Ala Phe Lys Gly Val Trp Thr Gln
            20                  25                  30

Ala Phe Trp Lys Ala Val Thr Ala Glu Phe Leu Ala Met Leu Ile Phe
        35                  40                  45
```

```
Val Leu Leu Ser Leu Gly Ser Thr Ile Asn Trp Gly Gly Thr Glu Lys
    50                  55                  60

Pro Leu Pro Val Asp Met Val Leu Ile Ser Leu Cys Phe Gly Leu Ser
65                  70                  75                  80

Ile Ala Thr Met Val Gln Cys Phe Gly His Ile Ser Gly Gly His Ile
                85                  90                  95

Asn Pro Ala Val Thr Val Ala Met Val Cys Thr Arg Lys Ile Ser Ile
                100                 105                 110

Ala Lys Ser Val Phe Tyr Ile Ala Ala Gln Cys Leu Gly Ala Ile Ile
            115                 120                 125

Gly Ala Gly Ile Leu Tyr Leu Val Thr Pro Ser Val Val Gly Gly
130                 135                 140

Leu Gly Val Thr Met Val His Gly Asn Leu Thr Ala Gly His Gly Leu
145                 150                 155                 160

Leu Val Glu Leu Ile Ile Thr Phe Gln Leu Val Phe Thr Ile Phe Ala
                165                 170                 175

Ser Cys Asp Ser Lys Arg Thr Asp Val Thr Gly Ser Ile Ala Leu Ala
            180                 185                 190

Ile Gly Phe Ser Val Ala Ile Gly His Leu Phe Ala Ile Asn Tyr Thr
            195                 200                 205

Gly Ala Ser Met Asn Pro Ala Arg Ser Phe Gly Pro Ala Val Ile Met
210                 215                 220

Gly Asn Trp Glu Asn His Trp Ile Tyr Trp Val Gly Pro Ile Ile Gly
225                 230                 235                 240

Ala Val Leu Ala Gly Gly Leu Tyr Glu Tyr Val Phe Cys Pro Asp Val
                245                 250                 255

Glu Phe Lys Arg Arg Phe Lys Glu Ala Phe Ser Lys Ala Ala Gln Gln
            260                 265                 270

Thr Lys Gly Ser Tyr Met Glu Val Glu Asp Asn Arg Ser Gln Val Glu
            275                 280                 285

Thr Asp Asp Leu Ile Leu Lys Pro Gly Val Val His Val Ile Asp Val
    290                 295                 300

Asp Arg Gly Glu Glu Lys Lys Gly Lys Asp Gln Ser Gly Glu Val Leu
305                 310                 315                 320

Ser Ser Val

<210> SEQ ID NO 2
<211> LENGTH: 208
<212> TYPE: PRT
<213> ORGANISM: Artificial sequence
<220> FEATURE:
<223> OTHER INFORMATION: Part from aquaporin-4

<400> SEQUENCE: 2

Met Ser Asp Arg Pro Thr Ala Arg Arg Trp Gly Lys Cys Gly Pro Leu
1               5                   10                  15

Cys Thr Arg Glu Asn Ile Met Val Ala Phe Lys Gly Val Trp Thr Gln
                20                  25                  30

Gly Pro Gly Pro Thr Ile Asn Trp Gly Gly Thr Glu Lys Pro Leu Pro
            35                  40                  45

Val Asp Gly Pro Gly Pro Gly Gly His Ile Asn Pro Ala Val Thr Val
    50                  55                  60

Ala Met Val Cys Thr Arg Lys Ile Ser Gly Pro Gly Pro Leu Val Thr
65                  70                  75                  80
```

```
Pro Pro Ser Val Val Gly Gly Leu Gly Val Thr Met Val His Gly Asn
            85                  90                  95
Gly Pro Gly Pro Cys Asp Ser Lys Arg Thr Asp Val Thr Gly Ser Ile
        100                 105                 110
Gly Pro Gly Pro Asn Pro Ala Arg Ser Phe Gly Pro Ala Val Ile Met
        115                 120                 125
Gly Asn Trp Glu Asn His Trp Gly Pro Gly Pro Asp Val Glu Phe Lys
        130                 135                 140
Arg Arg Phe Lys Glu Ala Phe Ser Lys Ala Ala Gln Gln Thr Lys Gly
145                 150                 155                 160
Ser Tyr Met Glu Val Glu Asp Asn Arg Ser Gln Val Gly Thr Asp Asp
                165                 170                 175
Leu Ile Leu Lys Pro Gly Val Val His Val Ile Asp Val Asp Arg Gly
                180                 185                 190
Glu Glu Lys Lys Gly Lys Asp Gln Ser Gly Glu Val Leu Ser Ser Val
                195                 200                 205

<210> SEQ ID NO 3
<211> LENGTH: 14
<212> TYPE: PRT
<213> ORGANISM: Artificial sequence
<220> FEATURE:
<223> OTHER INFORMATION: Part from aquaporin-4

<400> SEQUENCE: 3

Ser Asp Arg Pro Thr Ala Arg Arg Trp Gly Lys Cys Gly Pro
1               5                   10

<210> SEQ ID NO 4
<211> LENGTH: 10
<212> TYPE: PRT
<213> ORGANISM: Artificial sequence
<220> FEATURE:
<223> OTHER INFORMATION: Part from aquaporin-4

<400> SEQUENCE: 4

Gly Gly Thr Glu Lys Pro Leu Pro Val Asp
1               5                   10

<210> SEQ ID NO 5
<211> LENGTH: 7
<212> TYPE: PRT
<213> ORGANISM: Artificial sequence
<220> FEATURE:
<223> OTHER INFORMATION: Part from aquaporin-4

<400> SEQUENCE: 5

Cys Asp Ser Lys Arg Thr Asp
1               5

<210> SEQ ID NO 6
<211> LENGTH: 7
<212> TYPE: PRT
<213> ORGANISM: Artificial sequence
<220> FEATURE:
<223> OTHER INFORMATION: Part from aquaporin-4

<400> SEQUENCE: 6

Asn Pro Ala Arg Ser Phe Gly
1               5

<210> SEQ ID NO 7
<211> LENGTH: 14
```

```
<212> TYPE: PRT
<213> ORGANISM: Artificial sequence
<220> FEATURE:
<223> OTHER INFORMATION: Part from aquaporin-4

<400> SEQUENCE: 7

Glu Phe Lys Arg Arg Phe Lys Glu Ala Phe Ser Lys Ala Ala
1               5                   10

<210> SEQ ID NO 8
<211> LENGTH: 16
<212> TYPE: PRT
<213> ORGANISM: Artificial sequence
<220> FEATURE:
<223> OTHER INFORMATION: Part from aquaporin-4

<400> SEQUENCE: 8

Glu Phe Lys Arg Arg Phe Lys Glu Ala Phe Ser Lys Ala Ala Gln Gln
1               5                   10                  15

<210> SEQ ID NO 9
<211> LENGTH: 19
<212> TYPE: PRT
<213> ORGANISM: Artificial sequence
<220> FEATURE:
<223> OTHER INFORMATION: Part from aquaporin-4

<400> SEQUENCE: 9

Glu Phe Lys Arg Arg Phe Lys Glu Ala Phe Ser Lys Ala Ala Gln Gln
1               5                   10                  15

Thr Lys Gly

<210> SEQ ID NO 10
<211> LENGTH: 16
<212> TYPE: PRT
<213> ORGANISM: Artificial sequence
<220> FEATURE:
<223> OTHER INFORMATION: Part from aquaporin-4

<400> SEQUENCE: 10

Asp Val Asp Arg Gly Glu Glu Lys Lys Gly Lys Asp Gln Ser Gly Glu
1               5                   10                  15
```